(12) United States Patent
Licato et al.

(10) Patent No.: US 8,115,784 B2
(45) Date of Patent: Feb. 14, 2012

(54) SYSTEMS AND METHODS FOR DISPLAYING MULTI-ENERGY DATA

(75) Inventors: Paul Licato, Wauwatosa, WI (US); Darin Okerlund, Muskego, WI (US); Sardar Mal Gautham, Waukesha, WI (US); Brian Thomsen, Milwaukee, WI (US); Bradley Gabrielse, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 620 days.

(21) Appl. No.: 12/323,727

(22) Filed: Nov. 26, 2008

(65) Prior Publication Data

US 2010/0131885 A1    May 27, 2010

(51) Int. Cl.
  *G09G 5/00*    (2006.01)
  *G09G 5/02*    (2006.01)
(52) U.S. Cl. ..................................... 345/634; 345/592
(58) Field of Classification Search ................... None
  See application file for complete search history.

(56) References Cited

U.S. PATENT DOCUMENTS

| | | | | |
|---|---|---|---|---|
| 4,149,081 | A * | 4/1979 | Seppi | 378/5 |
| 4,856,528 | A * | 8/1989 | Yang et al. | 382/131 |
| 5,506,785 | A * | 4/1996 | Blank et al. | 700/98 |
| 6,996,261 | B2 * | 2/2006 | deCharms | 382/131 |
| 7,072,501 | B2 * | 7/2006 | Wood et al. | 382/132 |
| 2001/0036304 | A1 * | 11/2001 | Yang et al. | 382/132 |
| 2003/0095697 | A1 * | 5/2003 | Wood et al. | 382/131 |
| 2003/0167001 | A1 * | 9/2003 | Allain et al. | 600/425 |
| 2007/0003124 | A1 * | 1/2007 | Wood et al. | 382/131 |
| 2008/0260092 | A1 | 10/2008 | Imai et al. | |
| 2010/0128844 | A1 | 5/2010 | Thomsen et al. | |

FOREIGN PATENT DOCUMENTS

| | | |
|---|---|---|
| EP | 1426903 A2 | 6/2004 |
| WO | 2005037074 A2 | 4/2005 |

OTHER PUBLICATIONS

Unofficial Translation of NL Search Report and Written Opinion from corresponding NL Application No. 2003843, on Apr. 22, 2011.

* cited by examiner

*Primary Examiner* — Ryan R Yang
(74) *Attorney, Agent, or Firm* — McAndrews, Held & Malloy, Ltd.; Rick Wascher

(57) ABSTRACT

Systems, methods and computer instructions for displaying multi-energy data are provided. Certain methods include: receiving multi-energy data from an operably connected data source; displaying the multi-energy data as an image via a graphical user interface; selecting a region of interest in the displayed image; and displaying information regarding the region of interest via the graphical user interface. Certain methods include: (1) displaying a graph that includes an attenuation line depicting radiodensity versus energy level; (2) displaying a material density graph of a region of interest and/or of results of segmenting a region of interest; and/or (3) displaying information in a window configured to be movable about an interface. Certain methods include: receiving multi-energy data from an operably connected data source; and displaying the multi-energy data as a fused image via a graphical user interface.

23 Claims, 6 Drawing Sheets

SYSTEMS AND METHODS FOR DISPLAYING MULTI-ENERGY DATA

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

Typically, in computed tomography (CT) imaging systems, an x-ray source emits a fan-shaped or a cone-shaped x-ray beam toward a subject or object, such as a patient or a piece of luggage, positioned on a support. The beam, after being attenuated by the subject, impinges upon a detector assembly. The intensity of the attenuated x-ray beam received at the detector assembly is typically dependent upon the attenuation of the x-ray beam by the subject.

In known third generation CT systems, the x-ray source and the detector assembly are rotated on a rotatable gantry portion around the object to be imaged so that a gantry angle at which the fan-shaped x-ray beam intersects the object constantly changes. The detector assembly is typically made of a plurality of detector modules. Data representing the intensity of the received x-ray beam at each of the detector elements is collected across a range of gantry angles. The data are ultimately processed to form an image.

Conventional CT systems emit an x-ray with a polychromatic spectrum. The x-ray attenuation of each material in the subject depends on the energy of the emitted x-ray. Due to this relationship, images acquired with a polychromatic x-ray beam suffer from beam hardening artifacts. CT projection data that is acquired with a monochromatic x-ray beam does not suffer from beam hardening artifacts.

If CT projection data is acquired at multiple x-ray energy levels, it is possible to create images largely free from beam hardening artifacts that look like they were acquired with a monochromatic x-ray beam. Additionally, the CT projection data that is acquired at multiple x-ray energy levels contains additional information about the subject or object being imaged that is not contained within a conventional CT image.

Dual energy projection data can be used to reconstruct images using basis material decomposition (BMD) algorithms. The generated images are representative of a pair of selected basis material densities. An example basis pair would be water and iodine. Unlike conventional CT images that are expressed in Hounsfield units (HU), material density images are expressed in mass per unit volume.

In addition to material density images, dual energy projection data can be used to produce a new image with x-ray attenuation coefficients equivalent to a chosen monochromatic energy. Such a monochromatic image includes an image where the intensity values of the voxels are assigned as if a CT image were created by collecting projection data from the subject with a monochromatic x-ray beam.

Given a pair of material density images, it is possible to generate other basis material image pairs. For example, from a water and iodine image of the same anatomy, it is possible to generate a different pair of material density images such as calcium and gadolinium. Similarly, from a pair of basis material images, it is possible to generate a pair of monochromatic images, each at a specific energy. The inverse is also possible, i.e. from a pair of monochromatic images, a pair of basis material image pairs can be derived, or a pair of monochromatic images at different energies. Effective-Z images are a third type of image that can be derived from a pair of material density or monochromatic images. An effective-Z image displays the average atomic number of the material contained within a given image voxel.

While known systems and methods can be employed to create and display material density images, monochromatic images, and/or effective-Z images. Known systems and methods are not equipped to provide clinical insight into relationships among such images. Further, known systems and methods simply display images created using dual energy data, and are lacking in regard to user interaction and analysis.

Dual energy data is commonly procured, stored and accessed in healthcare environments. Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during and/or after surgery, medical personnel may access patient information, such as images of a patient's anatomy, that are stored in a medical information system. Radiologists, cardiologists and/or other clinicians may review stored images and/or other information, for example.

Using a PACS and/or other workstation, a clinician, such as a radiologist or cardiologist, for example, may perform a variety of activities, such as an image reading, to facilitate a clinical workflow. A reading, such as a radiology or cardiology procedure reading, is a process of a healthcare practitioner, such as a radiologist or a cardiologist, viewing digital images of a patient. The practitioner performs a diagnosis based on a content of the diagnostic images and reports on results electronically (e.g., using dictation or otherwise) or on paper. The practitioner, such as a radiologist or cardiologist, typically uses other tools to perform diagnosis. Some examples of other tools are prior and related prior (historical) exams and their results, laboratory exams (such as blood work), allergies, pathology results, medication, alerts, document images, and other tools. For example, a radiologist or cardiologist typically looks into other systems such as laboratory information, electronic medical records, and healthcare information when reading examination results.

Improved systems and methods for analysis of multi-energy data are desirable, particularly in healthcare environments, where dual energy data, a type of multi-energy data, is commonly procured.

BRIEF SUMMARY OF THE INVENTION

Certain embodiments of the present technology provide systems, methods and computer instructions for displaying multi-energy data, such as dual energy data, for example.

In certain embodiments, for example, a method for displaying multi-energy data includes: receiving multi-energy data from an operably connected data source; displaying the multi-energy data as an image via a graphical user interface; selecting a region of interest in the displayed image; and displaying information regarding the region of interest via the graphical user interface.

In certain embodiments, for example, a system for displaying multi-energy data includes: a data source including multi-energy data; a graphical user interface; and a processor operably connected to the data source and the graphical user interface, wherein the processor allows multi-energy data to be retrieved from the data source, wherein the processor allows the multi-energy data to be displayed as an image on the graphical user interface, wherein the processor allows a region of interest in the displayed image to be selected, and wherein the processor allows information regarding the region of interest to be displayed on the graphical user interface.

In certain embodiments, for example, a computer-readable storage medium including a set of instructions for execution on a processing device and associated processing logic includes: a routine that allows multi-energy data to be received from an operably connected data source; a routine that allows the multi-energy data to be displayed as an image via a graphical user interface; a routine that allows a region of interest in the displayed image to be selected; and a routine that allows information regarding the region of interest to be displayed via the graphical user interface.

In certain embodiments, for example, a method for displaying multi-energy data includes: receiving multi-energy data from an operably connected data source; and displaying the multi-energy data as a fused image via a graphical user interface, wherein the fused image provides visual information based on a first multi-energy data representation and a second multi-energy data representation.

Figure 1:
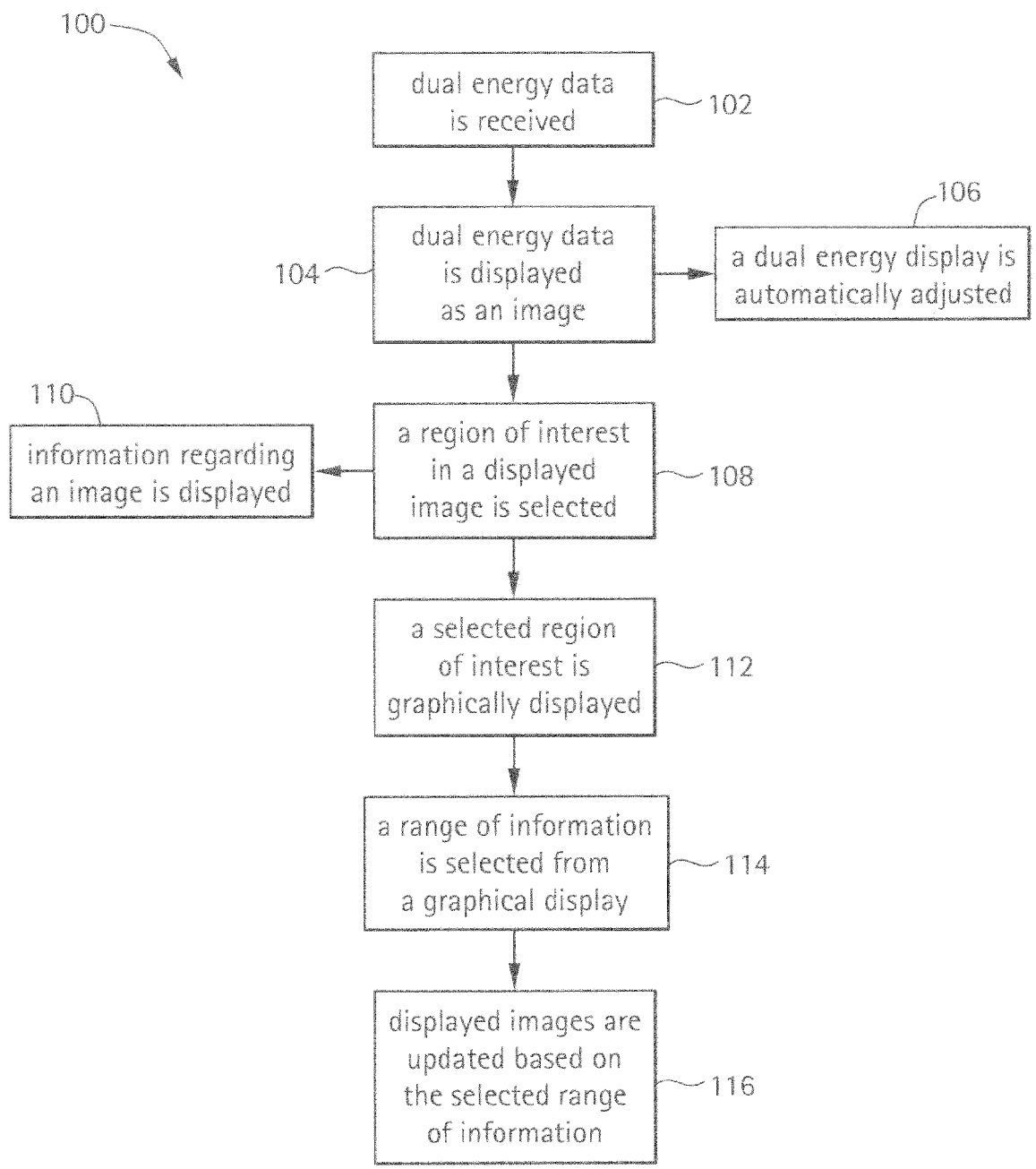
FIG. 1 is a flow diagram that illustrates a method used in accordance with an embodiment of the present technology.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Certain embodiments of the present technology provide systems, methods and computer instructions for displaying multi-energy data, such as dual energy data, for example. Certain multi-energy data can be used in spectral imaging systems, such as photon counting systems, for example. Dual energy data, which is a type of multi-energy data, can be embodied in monochromatic images, material density images and/or effective-Z images. While many of the embodiments described herein are discussed in connection with dual energy data, the inventions described herein are not limited to dual energy data embodiments and can be used in connection with other types of multi-energy data, as one skilled in the art will appreciate. While many of the embodiments discussed herein discuss material density images for water and iodine, material density images for other materials can also be used, as one skilled in the art will appreciate. While many of the embodiments discussed herein include a user interface with a control panel and four quadrants, other user interface configurations can also be used, as one skilled in the art will appreciate. While many of the embodiments discussed herein describe a region of interest that can be selected in an image, a volume of interest and/or a pixel of interest can also be selected in an image, as one skilled in the art will appreciate.

FIG. 1 is a flow diagram that illustrates a method 100 used in accordance with an embodiment of the present technology. At 102, dual energy data is received. For example, dual energy data can be received at a workstation from data source, such as a CT system that acquires dual energy data and/or a database in which dual energy data is stored, for example.

At 104, dual energy data is displayed as an image. For example, dual energy data can be displayed graphically via a user interface of a workstation. In certain embodiments, dual energy data can be displayed as a monochromatic image, a material density image and/or an effective-Z image, for example. In certain embodiments, data can be displayed as a fused image as described below in connection with FIG. 5, for example.

At 106, a dual energy display is automatically adjusted. For example, certain embodiments of the present technology provide for automatic adjustment of a window that displays a monochromatic image, which images can be displayed at various energy levels. For example, when a monochromatic image is adjusted from a first energy level to a second energy level, window width and/or window level can be adjusted automatically to reflect the change in contrast in the image at the different energy levels. In certain embodiments, for example, a window width and/or window level can increase or decrease by a certain percent for every kiloelectronvolt (keV) change in energy level. In certain embodiments, for example, automatic adjustment of a window that displays a monochromatic image can be based on image characteristics. In certain embodiments, automatic adjustment of a window can be based on signal to noise, contrast to noise, standard deviation, and/or anatomy of interest, for example.

At 108, a region of interest in a displayed image is selected. For example, a region of interest can be selected at a workstation by highlighting the region of interest using input commands entered via a keyboard, mouse and/or touchscreen. In certain embodiments, a region of interest can also be selected automatically, for example, based on preferences associated with study information for the dual energy data. In certain embodiments, a region of interest can be pixel that is selected by hovering a cursor over the pixel.

At 110, information regarding an image is displayed. For example, information regarding an image can be displayed graphically via a user interface of a workstation. In certain embodiments, the information can be displayed in real time, for example, to provide an interactive user interface. In certain embodiments, real time can be shortly after the action that causes the information to be displayed. Certain embodiments of the present technology provide for displaying information regarding an image when a cursor points to an image. For example, source and/or processed dual energy data regarding an indicated portion of an image, such as a region of interest, for example, can be displayed. For example, when a cursor points to a monochromatic image, material densities for one or more material basis pairs for the indicated voxel and/or effective-z information can be displayed. For example, when a cursor points to a material density image, the material density in the paired image can be displayed. For example, when a cursor points to an effective-z image, monochromatic and/or material density information can be displayed.

In certain embodiments, information regarding an image can be displayed in a window configured to be movable about a user interface. In such embodiments, information regarding the portion of the image that is behind the window can be displayed in the window. When the window is moved, the information displayed therein can be updated based on the portion of the image that is behind the window. The information displayed in the window can include the information described above, for example. In certain embodiments, the information displayed in the window can be updated in real time, for example, to provide an interactive user interface. In certain embodiments, real time can be shortly after the action that causes the information to be updated. In certain embodiments, the window can be configured to roam, resize, change the type of data displayed in the window, zoom-in, zoom-out, change window level, synchronize with underlying data (for example, by updating the information displayed in the window based on a change of the image that is behind the window), display fusion parameters and/or compute and show stats on the selected region of the image, for example. In certain embodiments, the window can be configured to provide data as segmented masks, contours, histograms, and/or fused layers, for example.

Providing information regarding an image based on dual energy data can be useful, for example, to provide for a quality check of the image and/or aid in assessing material decomposition. For example, providing such information can provide for comparing monochromatic and polychromatic data to assess beam hardening and/or bowtie artifacts. For example, providing such information can provide for assessing material separation in material pair images, such as water and iodine images, for example, such that anatomy boundaries, such as the boundaries of an artery, for example, can be determined with increased accuracy. For example, providing such information can provide for assessing material separation in material pair images, such as calcium and iodine images, for example, such that anatomy boundaries, such as the boundaries of the skull bone, for example, can be determined with increased accuracy.

At 112, a selected region of interest is graphically displayed. For example, a selected region of interest can be displayed graphically via a user interface of a workstation. In certain embodiments, the selected region of interest can be displayed graphically in real time, for example, to provide an interactive user interface. In certain embodiments, real time can be shortly after the region of interest is selected. For example, as discussed in connection with FIG. 2, an attenuation line representing the selected region of interest can be displayed on a graph that also includes an attenuation line(s) of a known material(s) and/or another selected region(s) of interest. For example, as discussed in connection with FIG. 3, the region of interest can be segmented and the segmentation results displayed on a graph. For example, as discussed in connection with FIG. 4, the region of interest can be displayed on a graph that also displays a known material(s) and/or another selected region(s) of interest.

At 114, a range of information is selected from a graphical display. For example, a range of information can be selected at a workstation by highlighting the range of information using input commands entered via a keyboard, mouse and/or touchscreen. In certain embodiments, a range of information can also be selected automatically, for example, based on preferences associated with study information for the dual energy data. For example, as discussed in connection with FIGS. 3 and 4, the range of information selected can be a range of material densities.

At 116, displayed images are updated based on the selected range of information. For example, images displayed graphically via a user interface of a workstation can be updated based on the selected range of information. In certain embodiments, the images can be updated in real time, for example, to provide an interactive user interface. In certain embodiments, real time can be shortly after the action that causes the image to be updated. For example, as discussed in connection with FIGS. 3 and 4, portions of an image that depict material with a density that is within a selected density range can be highlighted.

One or more of the steps of the method 100 may be implemented alone or in combination in hardware, firmware, and/ or as a set of instructions in software, for example. Certain embodiments may be provided as a set of instructions residing on a computer-readable medium, such as a memory, hard disk, DVD, or CD, for execution on a general purpose computer or other processing device. For example, certain embodiments provide a computer-readable storage medium encoded with a set of instructions for execution on a processing device and associated processing logic, wherein the set of instructions includes a routine(s) configured to provide the functions described in connection with the method 100 described in connection with FIG. 1.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

Figure 2:
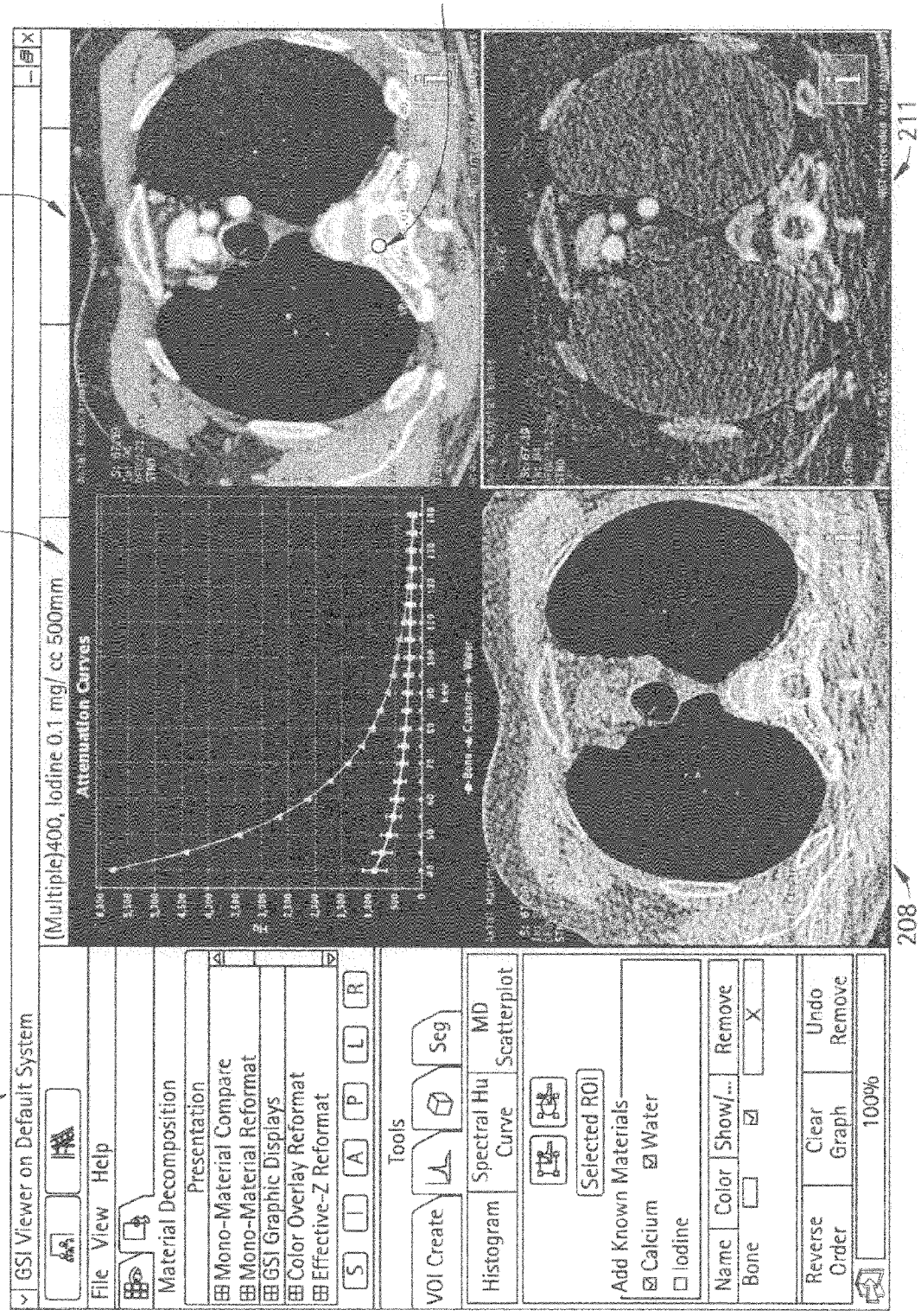
FIG. 2 depicts a user interface used in accordance with an embodiment of the present technology.

FIG. 2 depicts a user interface 200 used in accordance with an embodiment of the present technology. The user interface 200 includes a control panel 202 and four quadrants 204, 206, 208 and 211. The quadrants 208 and 211 include material density images for water and iodine, respectively, which images depict anatomy. The quadrant 206 includes a monochromatic image depicting the same anatomy. A region of interest 212 is specified in the monochromatic image. The specified region of interest 212 is bone. Other regions of interest can be selected in the monochromatic image in 206 and/or the material density images in 208 and 211. The quadrant 204 includes a graph depicting radiodensity in Hounsfield units (HU) as a function of energy in kiloelectronvolts (keV). The graph depicts attenuation lines for bone (the middle line), calcium (the upper line) and water (the lower line—on the x-axis at 0 HU). The calcium and water attenuation lines are selected in the control panel 202 as materials with known attenuation values. Other materials with known attenuation values, such as iodine, for example, can also be selected from the control panel 202 and selected known materials can be de-selected from the control panel 202. The bone attenuation line is included in the graph based on the region of interest 212 selected in the monochromatic image in 206. A selected region of interest can be changed and/or multiple regions of interest can be selected in the monochromatic image in 206 and/or the material density images in 208 and 211 such that an attenuation line(s) for any desired region(s) of interest can be included in the graph. Also, regions of interest can be selected for display in the graph or de-selected so as not to be displayed in the graph from the control panel 202. Thus, a graph including attenuation lines for a known material(s) and/or a material(s) selected in a region(s) of interest can be displayed. Such a graph can aid analysis of dual energy data, for example, by aiding identification of energy levels (in keV) at which the radiodensity of materials (in HU) are distinct. For example, as shown in FIG. 2, the radiodensity of bone and calcium is about the same at 120 keV. However, the radiodensity of bone and calcium is more distinct at 70 keV. Thus, a user may select to view a monochromatic image of anatomy at 70 keV (or less) if the user wants to be able to more clearly distinguish between bone and calcium.

Figure 3:
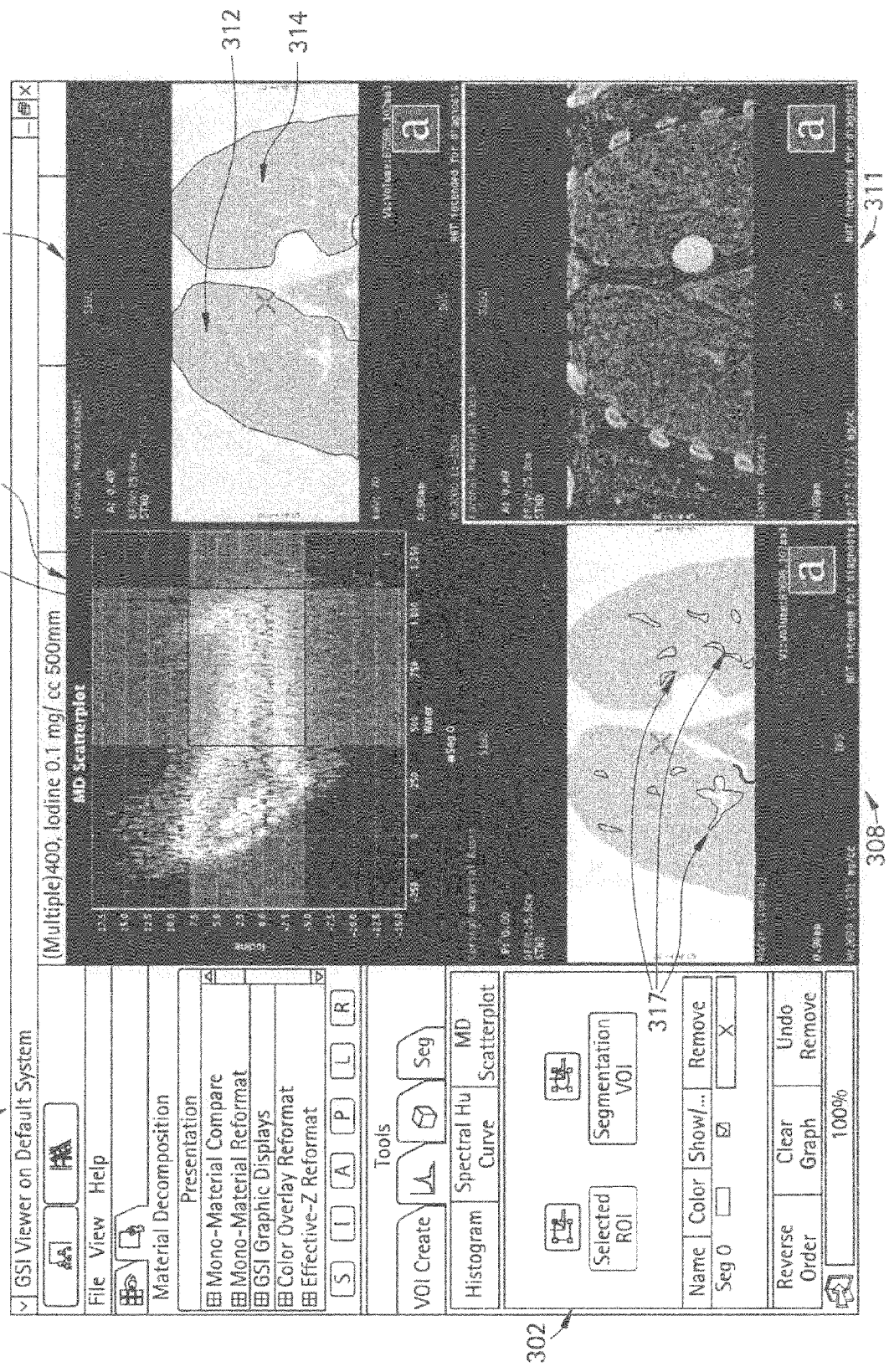
FIG. 3 depicts a user interface used in accordance with an embodiment of the present technology.

FIG. 3 depicts a user interface 300 used in accordance with an embodiment of the present technology. The user interface 300 includes a control panel 302 and four quadrants 304, 306, 308 and 311. The quadrants 308 and 311 include material density images for water and iodine, respectively, which images depict anatomy. The quadrant 306 includes a monochromatic image depicting the same anatomy. Regions of interest 312 and 314 are specified in the monochromatic image. The specified regions of interest 312 and 314 are lungs. Other regions of interest can be selected in the monochromatic image in 306 and/or the material density images in 308 and 311. The regions of interest 312 and 314 can be segmented utilizing an image segmentation algorithm. In certain embodiments, the segmentation algorithm can be fully automated, semi-automated or manual, for example. The segmentation results can be displayed as a material density graph that plots the segmentation results relative to the material density of two materials with known densities. As shown in the quadrant 304, segmentation results from segmenting regions of interest 312 and 314 are displayed as a material density graph that plots the segmentation results relative to the material density of iodine and water. A density range can be selected from such a graph, such as selection 316, for example. Material with a density that is within the selected density range can be highlighted in the monochromatic image in 306 and/or the material density images in 308 and 311. See, for example, the highlighted material 317 in the material density image in 308. Utilizing such a tool can aid analysis of dual energy data, for example, by aiding identification of material within an image that has a density within a specified range.

Figure 4:
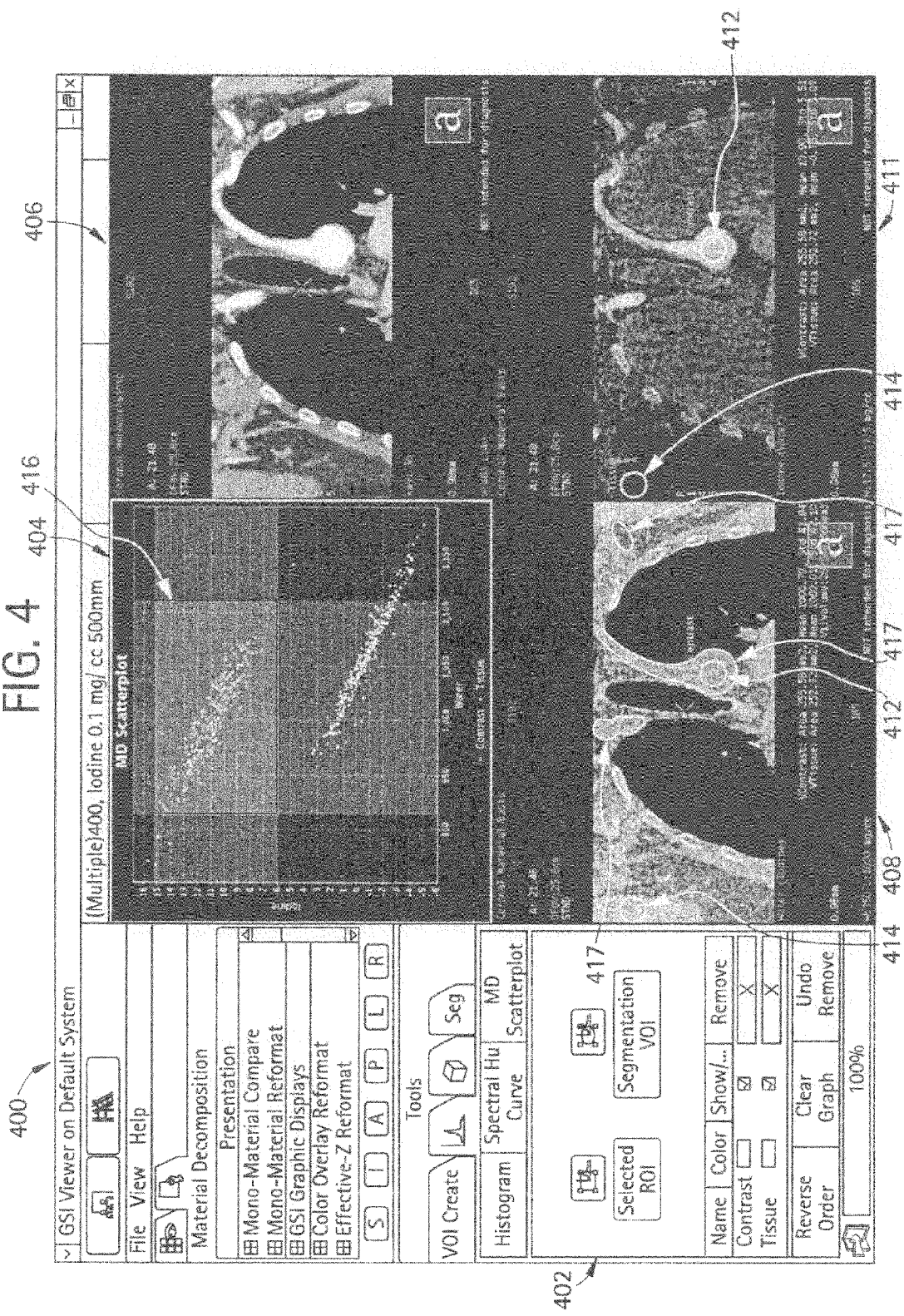
FIG. 4 depicts a user interface used in accordance with an embodiment of the present technology.

FIG. 4 depicts a user interface 400 used in accordance with an embodiment of the present technology. The user interface 400 includes a control panel 402 and four quadrants 404, 406, 408 and 411. The quadrant 406 includes a monochromatic image depicting anatomy. The quadrants 408 and 411 include material density images for water and iodine, respectively, which images depict the same anatomy. Regions of interest 412 and 414 are specified in the material density images. The specified regions of interest 412 and 414 are contrast and tissue, respectively. Other regions of interest can be selected in the monochromatic image in 406 and/or the material density images in 408 and 411. The densities of materials in the regions of interest 412 and 414 can be displayed as a material density graph that plots the material densities of the regions of interest relative to the material densities of two materials with known densities. As shown in the quadrant 404, densities of the materials in the regions of interest 412 and 414 are displayed as a material density graph that plots the material densities of the regions of interest relative to the material densities of iodine and water. In the graph, the contrast data is scattered in the upper portion of the graph and the tissue data is scattered in the lower portion of the graph. A density range can be selected from such a graph, such as selection 416, for example. Material with a density that is within the selected density range can be highlighted in the monochromatic image in 406 and/or the material density images in 408 and 411. See, for example, the highlighted material 417 in the material density image in 408. Utilizing such a tool can aid analysis of dual energy data, for example, by aiding identification of material within an image that has a density within a specified range.

Figure 5:
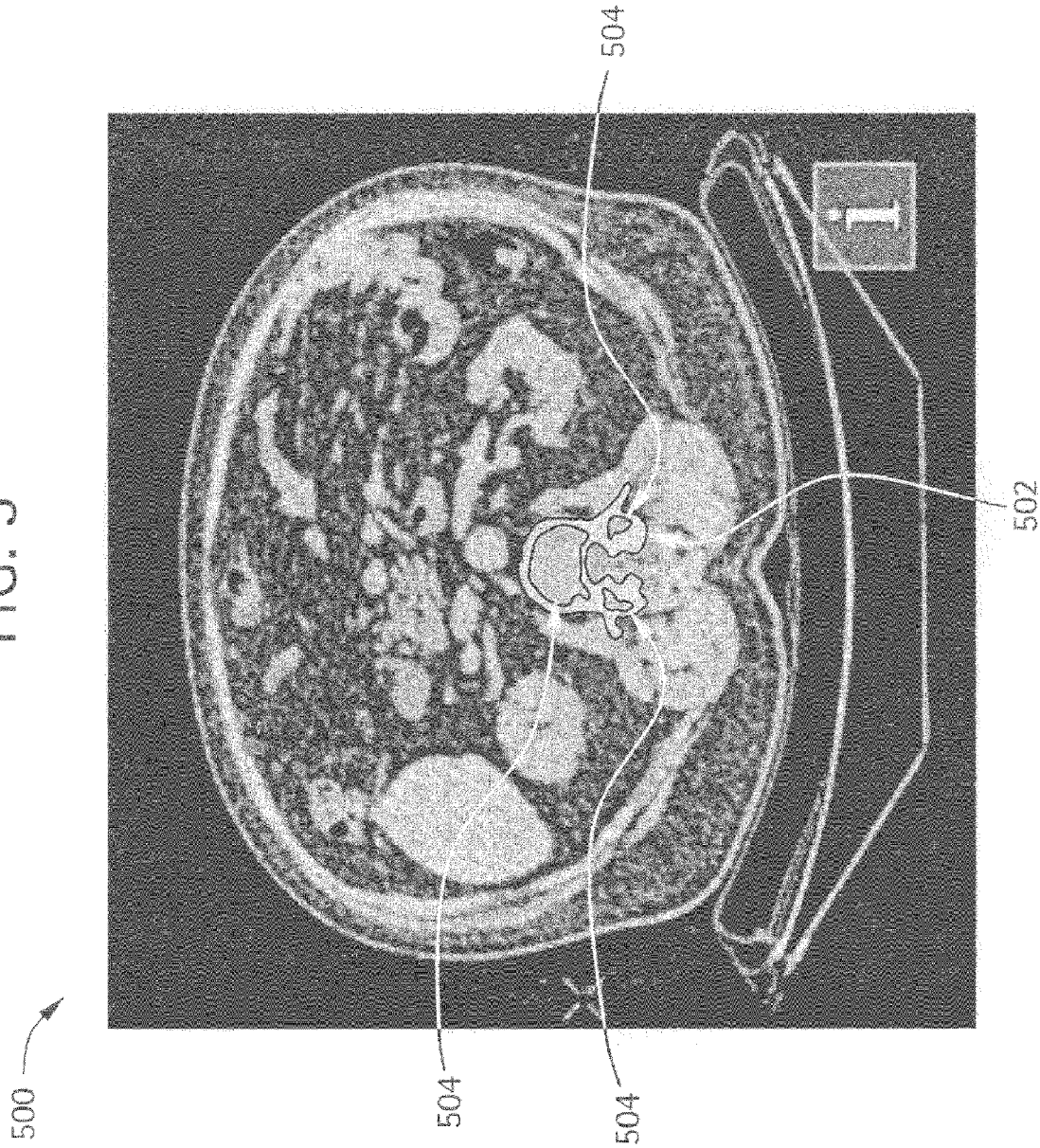
FIG. 5 depicts an image used in accordance with an embodiment of the present technology.

FIG. 5 depicts an image 500 used in accordance with an embodiment of the present technology. The image 500 is a fused image depicting anatomy, wherein a monochromatic image and a material density image(s) are combined. In the image 500, two material density images are overlaid on a monochromatic image. The first material density overlay is an iodine material density overlay that provides a first color in the portions of the image identified by 504. The second material density overlay is a water material density overlay that provides a second color in the portion of the image identified by 502 in certain embodiments, the order of the overlays and/or the opacity of the color provided in each overlay can be adjustable, for example, by a user in certain embodiments, any number of multi-energy data representations and any type of multi-energy data representations, such as material density images, monochromatic images and/or effective-z images, for example, can be used as overlays in a fused image in certain embodiments, fused images can provide a unified view of various multi-energy data representations, which can aid comparative analysis, for example. In certain embodiments, multi-energy data representations can comprise a range of color shades corresponding to a material property, such as density and/or atomic weight, for example.

Figure 6:
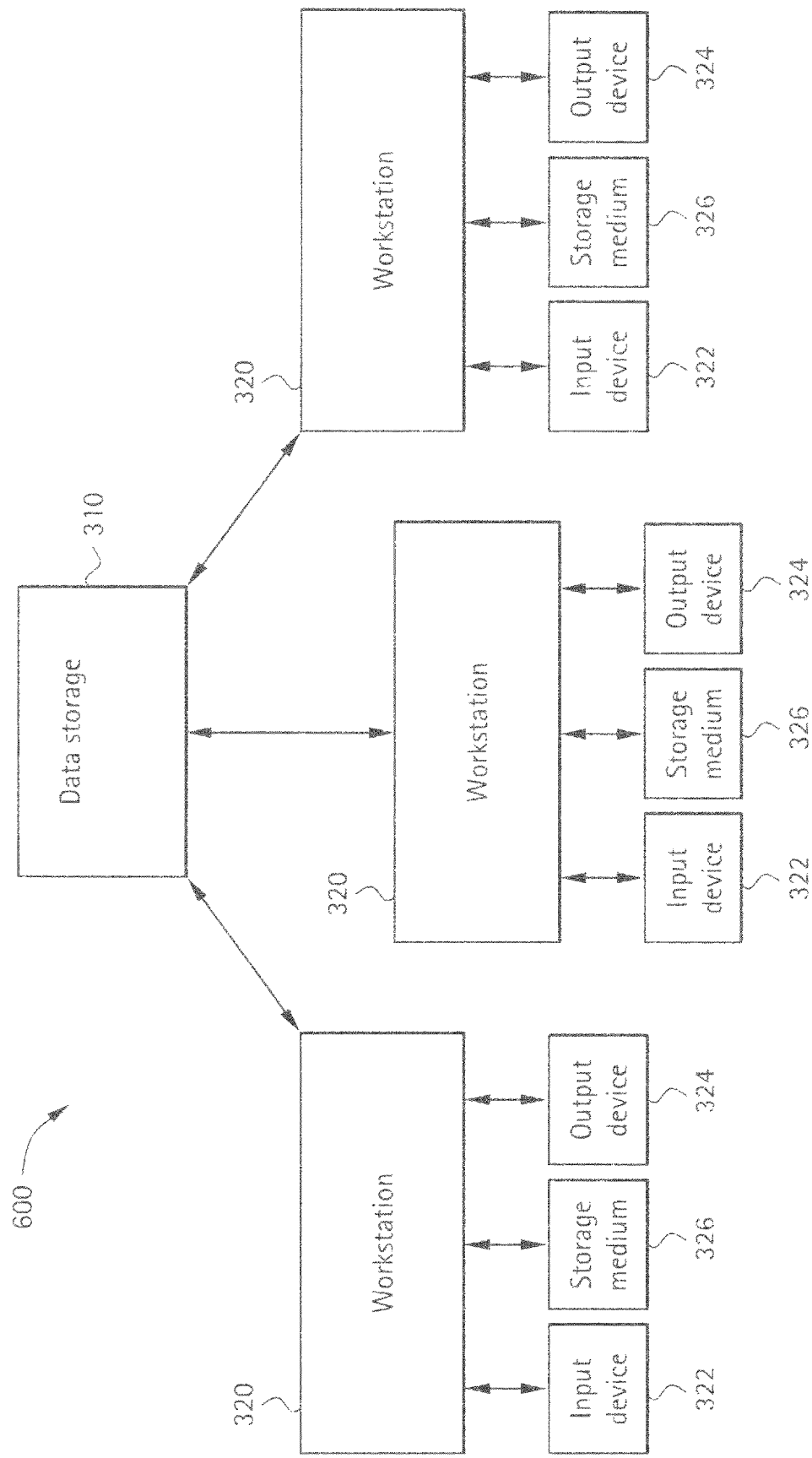
FIG. 6 depicts a clinical information system used in accordance with an embodiment of the present technology.

FIG. 6 depicts a clinical information system 600 used in accordance with embodiments of the present technology. Certain embodiments of the method 100 described above can be implemented on a clinical information system, such as the system 600. In certain embodiments, an interface including patient information and images may be viewed and/or constructed using a system such as system 600 including at least one data storage 310 and at least one workstation 320. While three workstations 320 are illustrated in system 600, a larger or smaller number of workstations 320 can be used in accordance with embodiments of the presently described technology. In addition, while one data storage 310 is illustrated in system 600, system 600 can include more than one data storage 310. For example, each of a plurality of entities (such as remote data storage facilities, hospitals or clinics) can each include one or more data stores 310 in communication with one or more workstations 320.

As illustrated in system 600, one or more workstations 320 can be in communication with at least one other workstation 320 and/or at least one data storage 310. Workstations 320 can be located in a single physical location or in a plurality of locations. Workstations 320 can be connected to and communicate via one or more networks.

Workstations 320 can be directly attached to one or more data stores 310 and/or communicate with data storage 310 via one or more networks. Each workstation 320 can be implemented using a specialized or general-purpose computer executing a computer program for carrying out the processes described herein. Workstations 320 can be personal computers or host attached terminals, for example. If workstations 320 are personal computers, the processing described herein can be shared by one or more data stores 310 and a workstation 320 by providing an applet to workstation 320, for example.

Workstations 320 include an input device 322, an output device 324 and a storage medium 326. For example, workstations 320 can include a mouse, stylus, microphone and/or keyboard as an input device. Workstations 320 can include a computer monitor, liquid crystal display ("LCD") screen, printer and/or speaker as an output device.

Storage medium 326 of workstations 320 is a computer-readable memory. For example, storage medium 326 can include a computer hard drive, a compact disc ("CD") drive, a USB thumb drive, or any other type of memory capable of storing one or more computer software applications. Storage medium 326 can be included in workstations 320 or physically remote from workstations 320. For example, storage medium 326 can be accessible by workstations 320 through a wired or wireless network connection.

Storage medium 326 includes a set of instructions for a computer. The set of instructions includes one or more routines capable of being run or performed by workstations 320. The set of instructions can be embodied in one or more software applications or in computer code.

Data storage 310 can be implemented using a variety of devices for storing electronic information such as a file transfer protocol ("FTP") server, for example. Data storage 310 includes electronic data. For example, data storage 310 can store patient exam images and/or other information, electronic medical records, patient orders, etc., for a plurality of patients. Data storage 310 may include and/or be in communication with one or more clinical information systems, for example.

Communication between workstations 320, workstations 320 and data storage 310, and/or a plurality of data stores 310 can be via any one or more types of known networks including a local area network ("LAN"), a wide area network ("WAN"), an intranet, or a global network (for example, Internet). Any two of workstations 320 and data stores 310 can be coupled to one another through multiple networks (for example, intranet and Internet) so that not all components of system 300 are required to be coupled to one another through the same network.

Any workstations 320 and/or data stores 310 can be connected to a network or one another in a wired or wireless fashion. In an example embodiment, workstations 320 and data store 310 communicate via the Internet and each workstation 320 executes a user interface application to directly connect to data store 310. In another embodiment, workstation 320 can execute a web browser to contact data store 310. Alternatively, workstation 320 can be implemented using a device programmed primarily for accessing data store 310.

Data storage 310 can be implemented using a server operating in response to a computer program stored in a storage medium accessible by the server. Data storage 310 can operate as a network server (often referred to as a web server) to communicate with workstations 320. Data storage 310 can handle sending and receiving information to and from workstations 320 and can perform associated tasks. Data storage 310 can also include a firewall to prevent unauthorized access and enforce any limitations on authorized access. For instance, an administrator can have access to the entire system and have authority to modify portions of system 600 and a staff member can only have access to view a subset of the data stored at data store 310. In an example embodiment, the administrator has the ability to add new users, delete users and edit user privileges. The firewall can be implemented using conventional hardware and/or software.

Data store 310 can also operate as an application server. Data store 310 can execute one or more application programs to provide access to the data repository located on data store 310. Processing can be shared by data store 310 and workstations 320 by providing an application (for example, a java applet). Alternatively, data store 310 can include a stand-alone software application for performing a portion of the processing described herein. It is to be understood that separate servers may be used to implement the network server functions and the application server functions. Alternatively, the network server, firewall and the application server can be implemented by a single server executing computer programs to perform the requisite functions.

The storage device located at data storage 310 can be implemented using a variety of devices for storing electronic information such as an FTP server. It is understood that the storage device can be implemented using memory contained in data store 310 or it may be a separate physical device. The storage device can include a variety of information including a data warehouse containing data such as patient medical data, for example.

Data storage 310 can also operate as a database server and coordinate access to application data including data stored on the storage device. Data storage 310 can be physically stored as a single database with access restricted based on user characteristics or it can be physically stored in a variety of databases.

In an embodiment, data storage 310 is configured to store data that is recorded with or associated with a time and/or date stamp. For example, a data entry can be stored in data storage 310 along with a time and/or date at which the data was entered or recorded initially or at data storage 310. The time/date information can be recorded along with the data as, for example, metadata. Alternatively, the time/date information can be recorded in the data in manner similar to the remainder of the data. In another alternative, the time/date information can be stored in a relational database or table and associated with the data via the database or table.

In an embodiment, data storage 310 is configured to store image and/or other medical data for a patient. The medical data can include data such as numbers and text. The medical data can also include information describing medical events. For example, the medical data/events can include a name of a medical test performed on a patient. The medical data/events can also include the result(s) of a medical test performed on a patient. For example, the actual numerical result of a medical test can be stored as a result of a medical test. In another example, the result of a medical test can include a finding or analysis by a caregiver that IS entered as text.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, mini-computers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method for displaying multi-energy data comprising:
receiving multi-energy data from an operably connected data source;
displaying the multi-energy data as an image via a graphical user interface;
selecting a region of interest in the displayed image; and
displaying information regarding the region of interest via the graphical user interface, wherein the information is displayed as a graph.

2. The method of claim 1, wherein information regarding the region of interest is displayed in real-time.

3. The method of claim 1, wherein the graph includes an attenuation line depicting radiodensity versus energy level for the selected region of interest.

4. The method of claim 3, wherein the graph further includes an attenuation line depicting radiodensity versus energy level for a known material.

5. The method of claim 1, wherein the graph is a material density graph of the region of interest.

6. The method of claim 1, wherein the graph is a material density graph of the results of segmenting the region of interest.

7. The method of claim 6, wherein the region of interest is segmented automatically.

8. The method of claim 1, wherein the multi-energy data is displayed as a monochromatic image, and wherein displaying information regarding the region of interest includes displaying at least one of effective-z information and material densities for one or more material basis pairs.

9. The method of claim 1, wherein the multi-energy data is displayed as a material density image, and wherein displaying information regarding the region of interest includes displaying the material density of a paired image.

10. The method of claim 1, wherein the multi-energy data is displayed as an effective-Z image, and wherein displaying information regarding the region of interest includes displaying at least one of monochromatic image information and material density image information.

11. The method of claim 1, comprising selecting a range of information from the graph.

12. The method of claim 11, further including updating a displayed image based on the selected range of information.

13. The method of claim 12, wherein the image is updated in real-time.

14. The method of claim 12, wherein the range of information is a range of material densities, and wherein updating a displayed image includes highlighting a portion of the image that depicts material with a density range within the selected range.

15. The method of claim 1, further including automatically adjusting the displayed image.

16. The method of claim 15, wherein the image is a monochromatic image, and wherein at least one of a window width and window level are automatically adjusted when the image is adjusted from a first energy level to a second energy level.

17. The method of claim 1, wherein displaying information regarding the region of interest includes displaying information in a window configured to be movable about the user interface, and wherein the information displayed in the window is based on the portion of the image that is behind the window.

18. The method of claim 17, wherein information displayed in the window updated in real-time when the window is moved.

19. A non-transitory computer-readable storage medium encoded with a set of instructions for execution on a processing device and associated processing logic for displaying multi-energy data, the set of instructions comprising:

a routine that allows multi-energy data to be received from an operably connected data source;

a routine that allows the multi-energy data to be displayed as an image via a graphical user interface;

a routine that allows a region of interest in the displayed image to be selected; and a routine that allows information regarding the region of interest to be displayed via the graphical user interface, wherein the information is displayed as a graph.

20. The medium and instructions of claim 19, wherein displaying information regarding the region of interest includes at least one of:

displaying a graph that includes an attenuation line depicting radiodensity versus energy level for the selected region of interest;

displaying a material density graph of the region of interest; and displaying a material density graph of the results of segmenting the region of interest.

21. A method for displaying multi-energy data comprising:

receiving multi-energy data from an operably connected data source; and displaying the multi-energy data as a fused image via a graphical user interface, wherein the fused image provides visual information based on a first multi-energy data representation comprising a first layer with an opacity and a second multi-energy data representation comprising a second layer with an opacity, wherein the layers are ordered, and wherein layer order is adjustable.

22. The method of claim 21, wherein the multi-energy data representations include at least one of a monochromatic image, a material density image and an effective-z image.

23. The method of claim 21, wherein each multi-energy data representation comprises a range of color shades corresponding to a material property.

* * * * *